United States Patent
Li et al.

(10) Patent No.: US 12,030,898 B2
(45) Date of Patent: Jul. 9, 2024

(54) ORGANIC ELECTROLUMINESCENT MATERIAL AND APPLICATION THEREOF IN OPTOELECTRONIC DEVICES

(71) Applicant: GUANGDONG AGLAIA OPTOELECTRONIC MATERIALS CO., LTD, Guangdong (CN)

(72) Inventors: Huiyang Li, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 562 days.

(21) Appl. No.: 17/297,871

(22) PCT Filed: Nov. 2, 2019

(86) PCT No.: PCT/CN2019/115176
§ 371 (c)(1),
(2) Date: May 27, 2021

(87) PCT Pub. No.: WO2020/119326
PCT Pub. Date: Jun. 18, 2020

(65) Prior Publication Data
US 2022/0033420 A1    Feb. 3, 2022

(30) Foreign Application Priority Data

Dec. 13, 2018  (CN) .......................... 201811524223.2

(51) Int. Cl.
| | | |
|---|---|---|
| *C07D 519/00* | (2006.01) | |
| *H10K 85/60* | (2023.01) | |
| *H10K 50/11* | (2023.01) | |
| *H10K 50/16* | (2023.01) | |

(52) U.S. Cl.
CPC ....... *C07D 519/00* (2013.01); *H10K 85/6572* (2023.02); *H10K 85/6574* (2023.02); *H10K 85/6576* (2023.02); *H10K 50/11* (2023.02); *H10K 50/16* (2023.02)

(58) Field of Classification Search
None
See application file for complete search history.

(56) References Cited

FOREIGN PATENT DOCUMENTS

| | | |
|---|---|---|
| CN | 104557875 A | 4/2015 |
| JP | 2008255324 A | 10/2008 |
| KR | 20100110495 A | 10/2010 |
| WO | 20140058183 A1 | 4/2014 |

*Primary Examiner* — Robert S Loewe
(74) *Attorney, Agent, or Firm* — Maschoff Brennan

(57) ABSTRACT

The invention provides an organic electroluminescent material and application thereof in optoelectronic devices. The organic electroluminescent material according to the invention having the structure of Formula (I), the compound of which contains a unit formed by imidazole and indenopyrrole, with its spiro structure molecule that is beneficial to inhibit the stacking between molecules. The compound has better thermal stability and will be applied to organic electroluminescent devices with characteristics such as luminous efficiency and color purity, has the potential to be applied to organic electroluminescent devices. The invention further provides an optoelectronic device including a cathode, an anode, and an organic layer. The organic layer is one or more of a hole injection layer, a hole transport layer, a light-emitting layer, a hole-blocking layer, an electron injection layer, and an electron transport layer. At least one layer of the organic layer contains the compound having Formula (I).

17 Claims, 1 Drawing Sheet

(I)

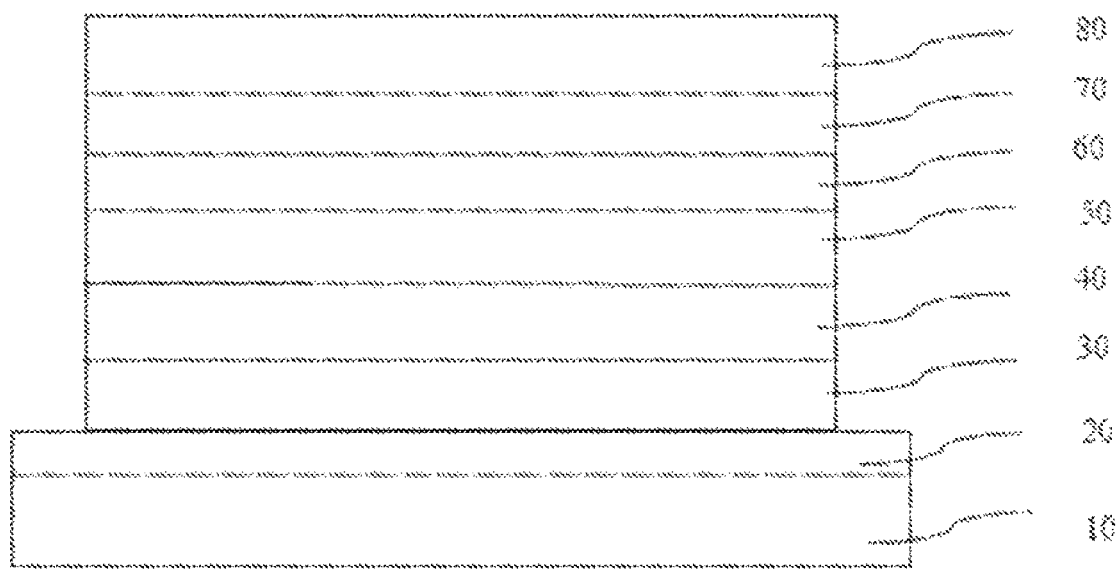

ORGANIC ELECTROLUMINESCENT MATERIAL AND APPLICATION THEREOF IN OPTOELECTRONIC DEVICES

FIELD OF THE INVENTION

The invention relates to the field of organic electroluminescent materials, in particular to luminescent material based on a unit formed by imidazole and indenopyrrole and an optoelectronic device thereof.

BACKGROUND

In recent years, organic light-emitting diodes (OLED), as a kind of lighting and display technology with huge application prospects, have received extensive attention from academia and industry. OLED devices have characteristics such as self-luminescence, wide viewing angle, short response time and ability to prepare flexible device, so they become a strong competitor of next-generation display and lighting technology. However, OLEDs still have problems such as low efficiency and short life span, which need to be further studied.

Since Forrest et al. reported on the electro-phosphorescent devices (PHOLED) in 1998, PHOLED have attracted attention because of their high-efficiently using triplet and singlet excitons to emit light. High-efficient PHOLED devices usually have a multilayer structure, and their advantage is that they can easily adjust the process such as carrier injection, transport, and recombination. The light-emitting layer usually adopts subject-object doping technology. When the object doping concentration is high, concentration quenching and $T_1$-$T_1$ annihilation will occur, resulting in a decrease in luminous efficiency. In order to solve these problems, the object material is usually doped into the subject material to "dilute" the concentration of the object material. The excitons formed in the subject are transferred to the object by means of Førster and Dexter energy transfer, and the excited object radiates light back to the ground state. Therefore, in order to obtain a high-efficient PHOLED device, it is particularly important to develop a new high-performance subject material.

The subject material in the light-emitting layer can be divided into three types: hole type, electron type and bipolar type. When the hole or electron type subject material with is used alone, on the one hand, it is easy to cause unbalanced charge transport in the light-emitting layer with reduced efficiency; on the other hand, that will cause the carrier recombination area to become narrow. The narrow carrier recombination will lead to local excitons, the density of which increases to accelerate $T_1$-$T_1$ annihilation, which is not conducive to the improvement of device performance. Bipolar material can effectively solve the above problems, not only can balance holes and electrons in the device, broaden the carrier recombination area, but also simplify the device structure, which is of great significance for optimizing the performance of organic optoelectronic devices.

SUMMARY

The purpose of the invention is to provide a bipolar organic electroluminescent material based on a unit formed by imidazole and indenopyrrole, with its spiro structure molecule that is beneficial to inhibit the stacking between molecules. The organic electroluminescent material according to the invention has better thermal stability, and balanced carrier transport performance, as well as high luminous efficiency and color purity.

An organic electroluminescent material has a compound with the structure of Formula (I):

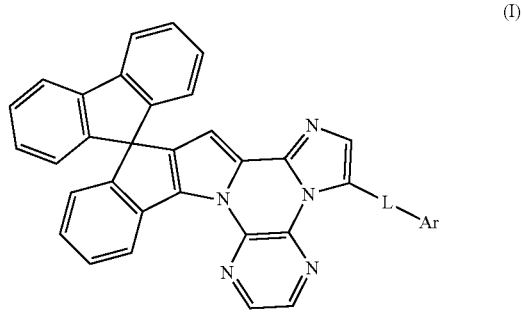

(I)

Wherein, L is a single bond, a substituted or unsubstituted phenylene group, a substituted or unsubstituted biphenylene group, or a substituted or unsubstituted pyridylene group.

Ar is one of the following groups:

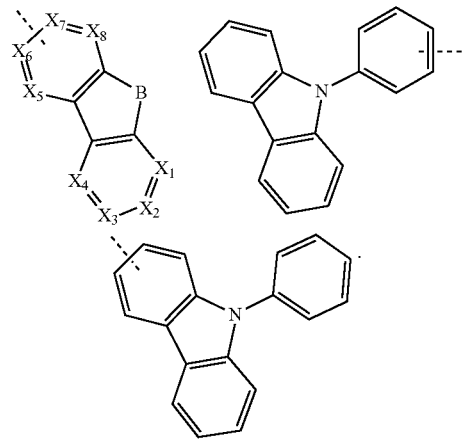

B is selected from O, S and Se.

$X_1$-$X_8$ are independently selected from N or CR, and each six-membered ring contains at most one N atom. R is independently selected from one of a hydrogen atom, a deuterium atom, halogen, an alkyl group, a heteroalkyl group, an aryl group, a heteroaryl group, an aryloxy group.

Preferably, L is a single bond, or a substituted or unsubstituted phenylene group.

Ar is one of the following groups:

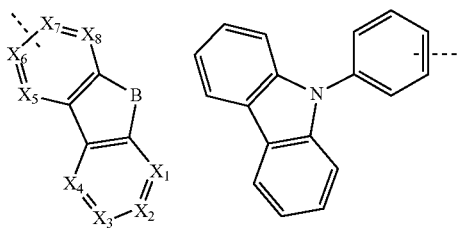

-continued

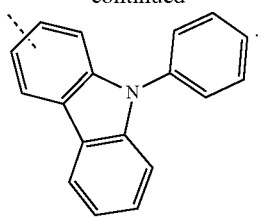

B is selected from O and S.

$X_1$-$X_8$ are independently selected from N or CR, and each six-membered ring contains at most one N atom. R is independently selected from one of a hydrogen atom, a deuterium atom, an alkyl group, and an aryl group.

Preferably, L is a single bond or a phenylene group.

Ar is one of the following groups:

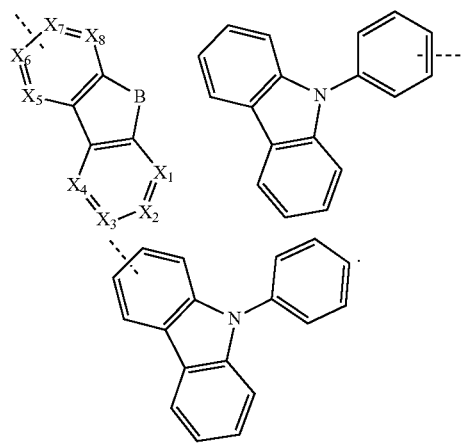

B is selected from O and S.

One of $X_1$-$X_8$ is N, and the rest are CH.

More preferably, L is a single bond.

Ar is one of the following groups:

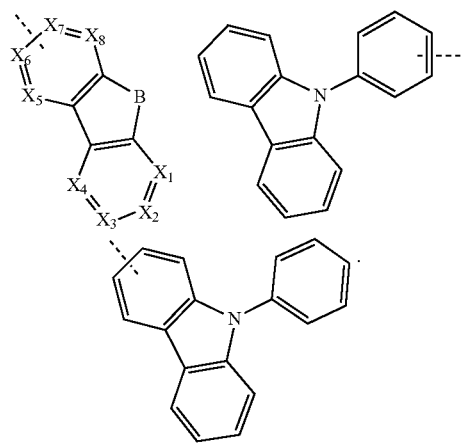

B is selected from O and S.

One of $X_1$-$X_8$ is N, and the rest are CH.

More preferably, L is a single bond.

Ar is one of the following groups:

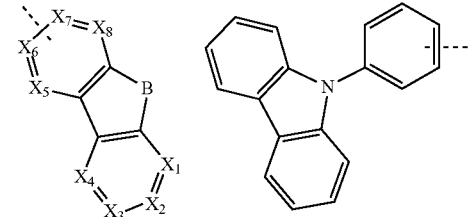
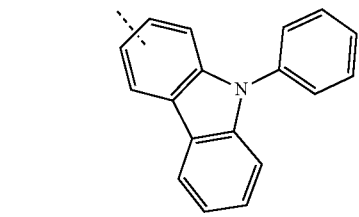
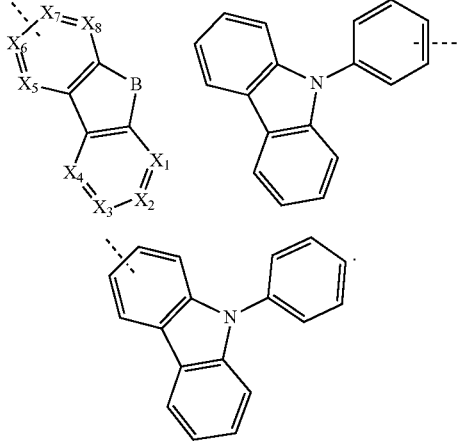

B is selected from O and S.

$X_1$-$X_8$ are CH.

Further preferably, the luminescent material represented by Formula (I) of the invention is the following Compounds 1-36, but not limited to the listed structures:

1

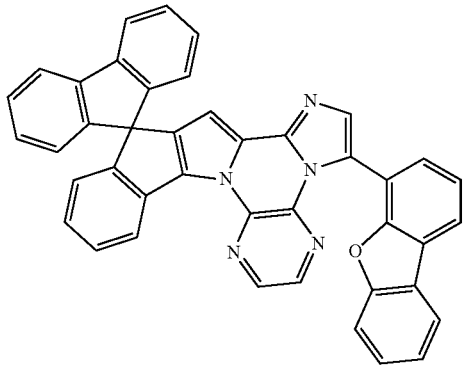

2

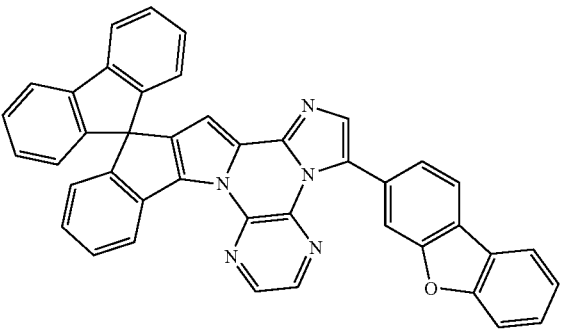

3
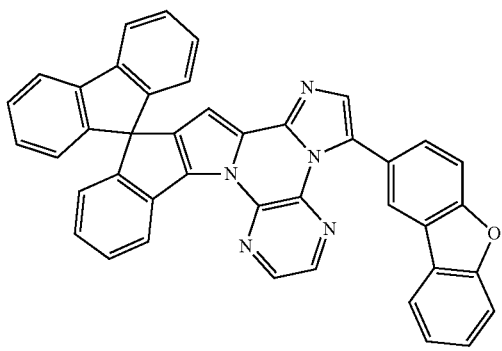
4
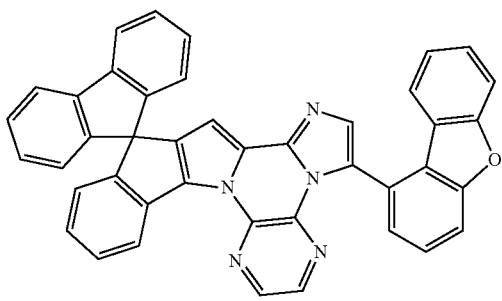
5
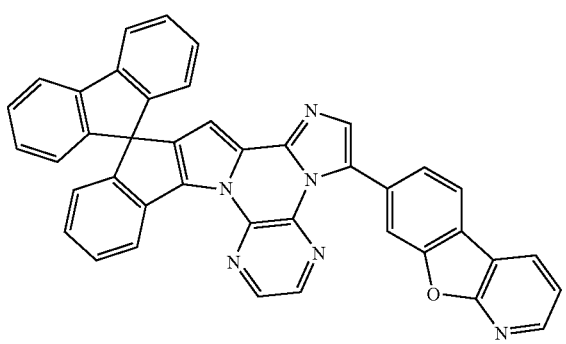
6
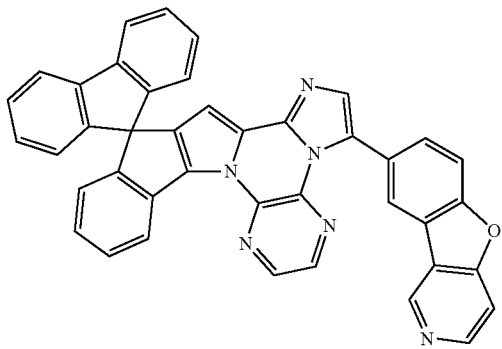
7
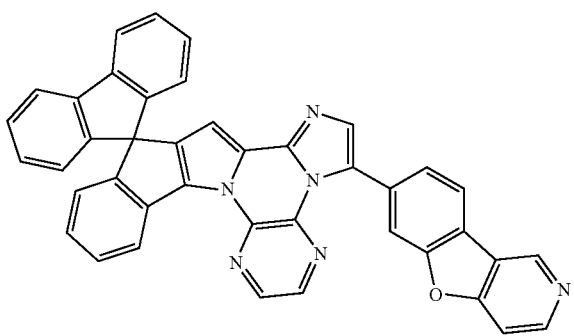
8
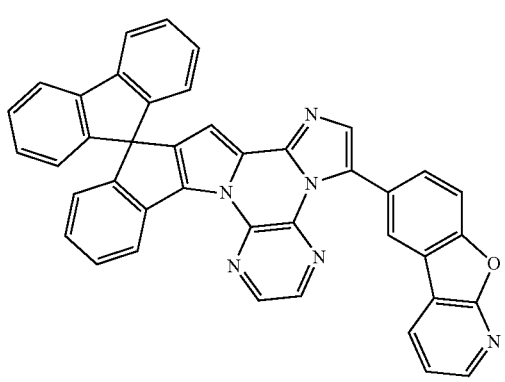
9
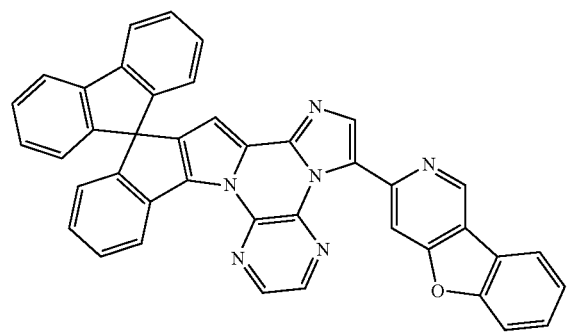
10
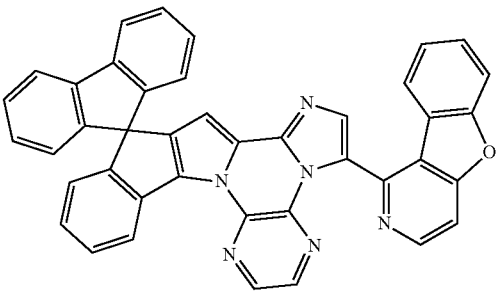

11
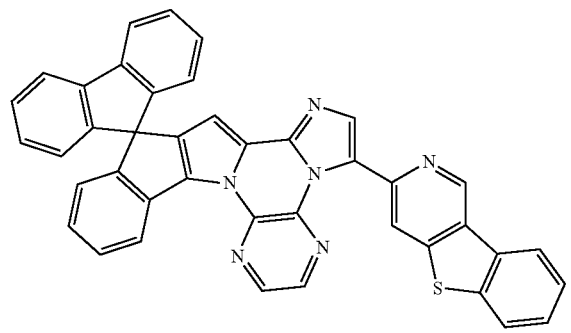
15
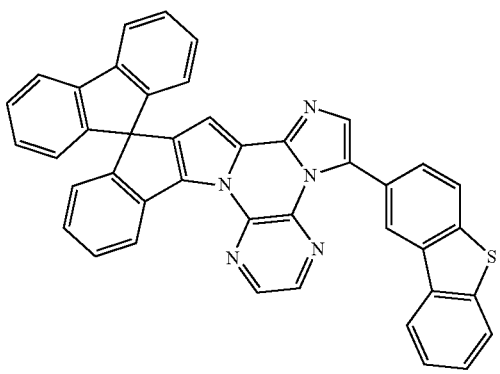
12
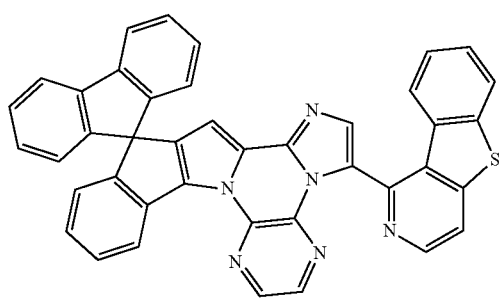
16
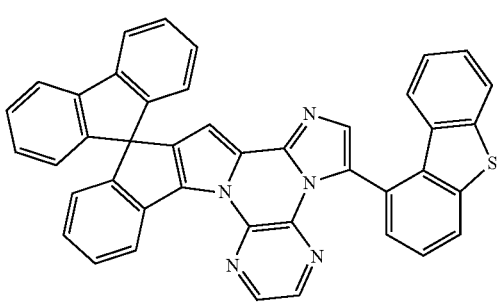
13
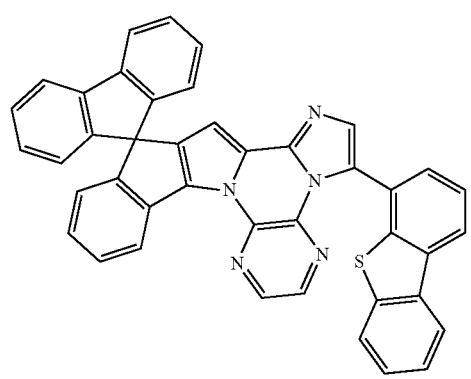
17
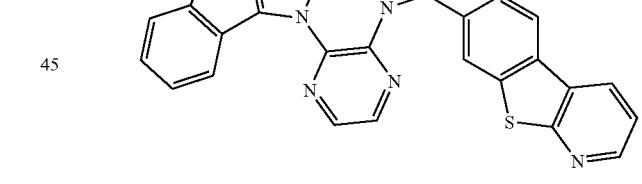
14
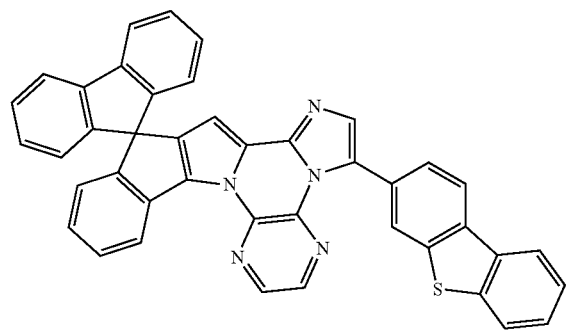
18
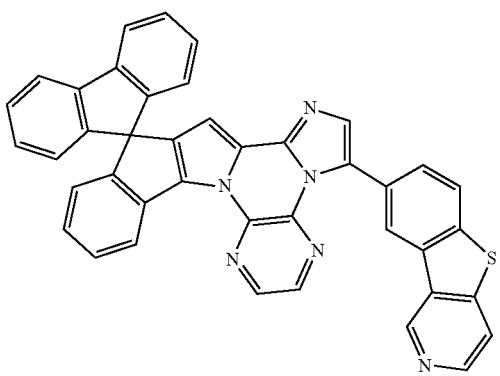

19
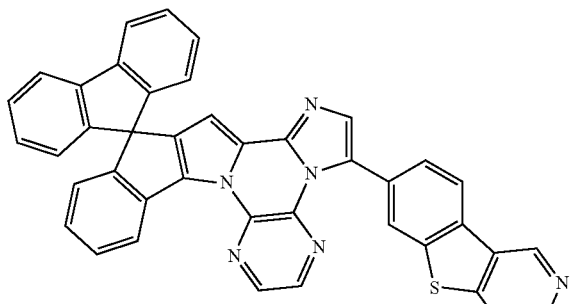
20
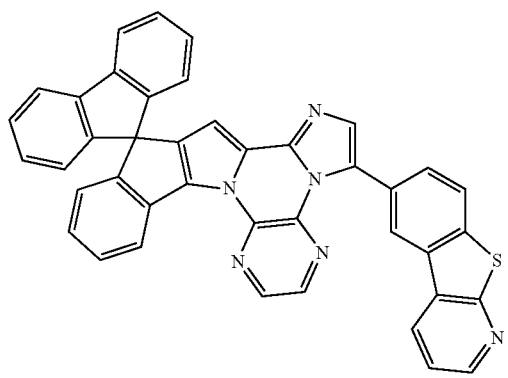
21
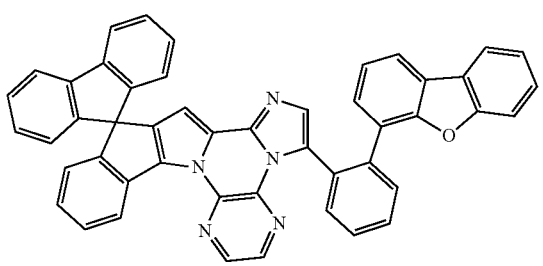
22
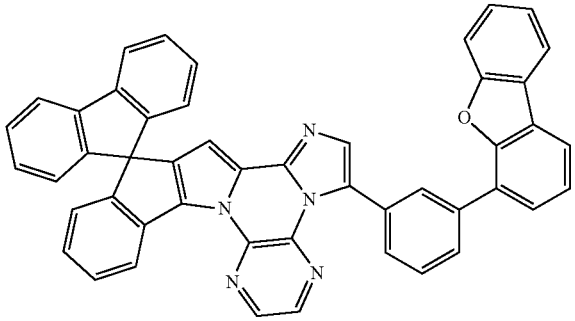
23
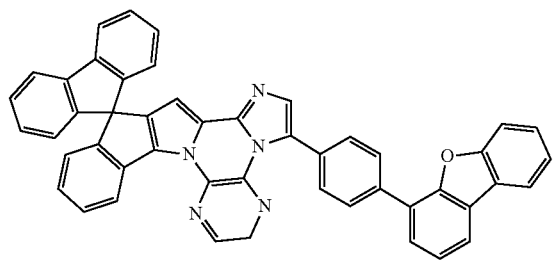
24
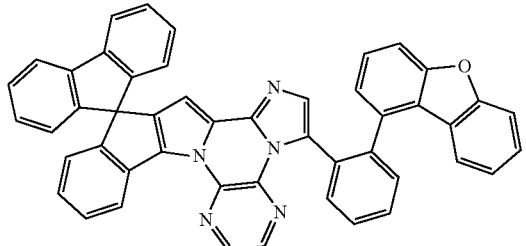
25
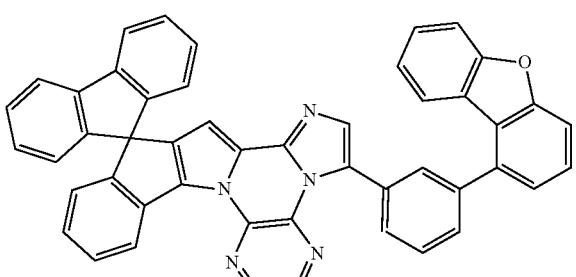
26
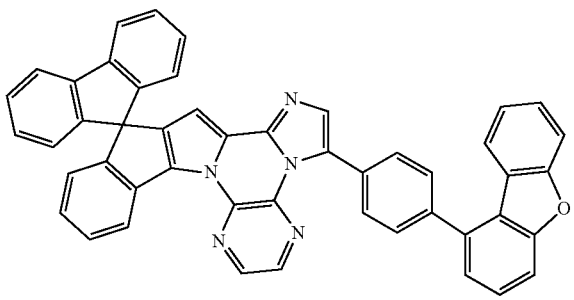
27
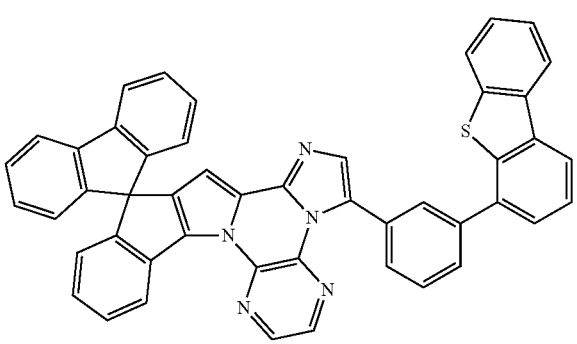
28
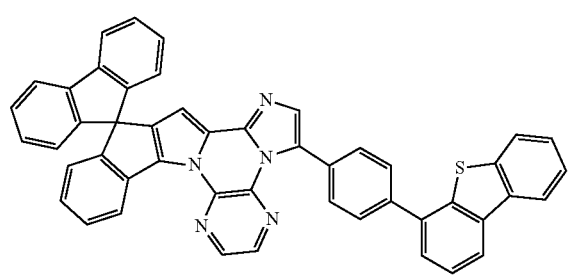

29
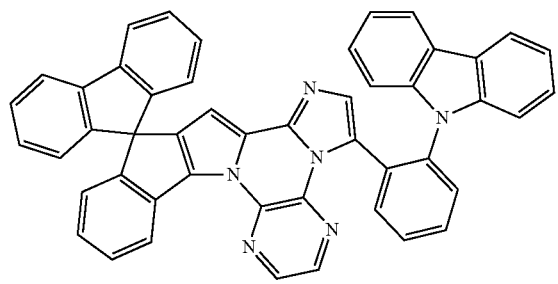
30
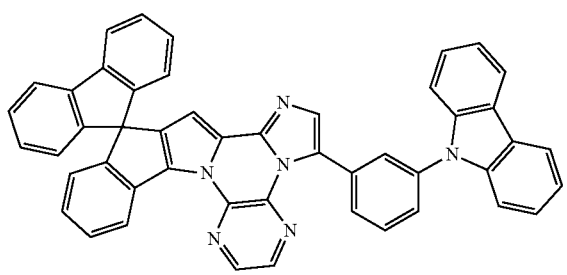
31
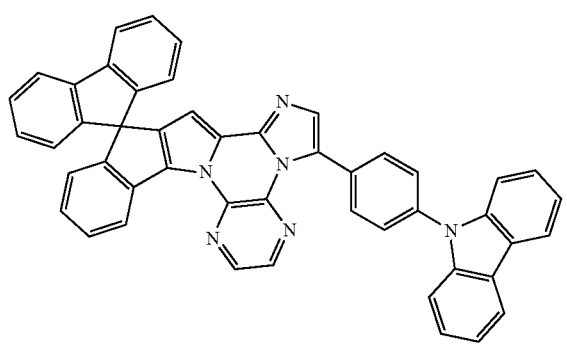
32
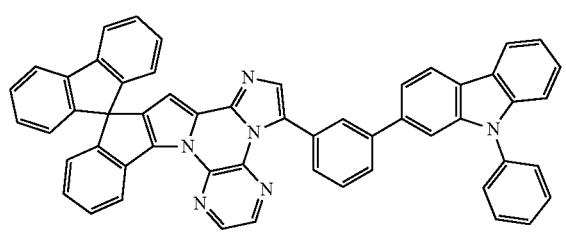
33
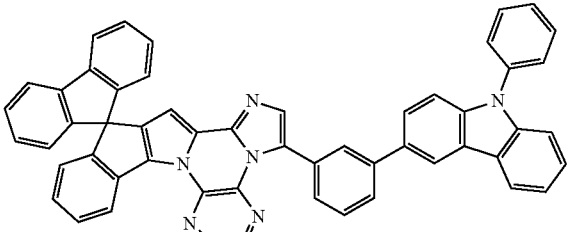
34
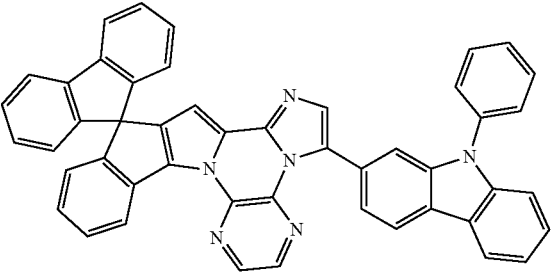
35
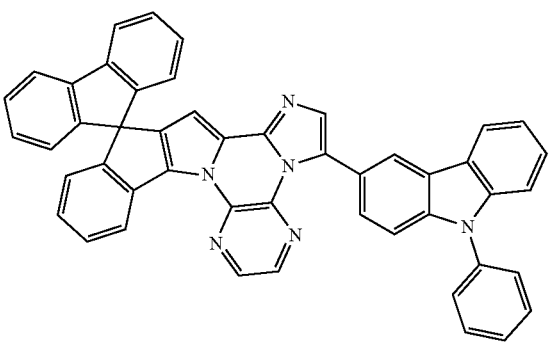
36
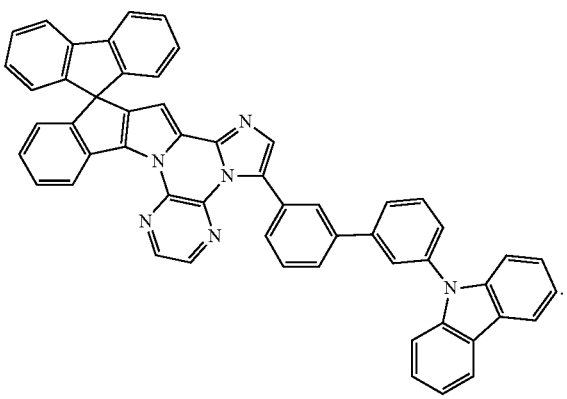
The synthesis method of the above compound includes the following steps:
S1: providing Compound a and Y-L-Ar, wherein Y is halogen;
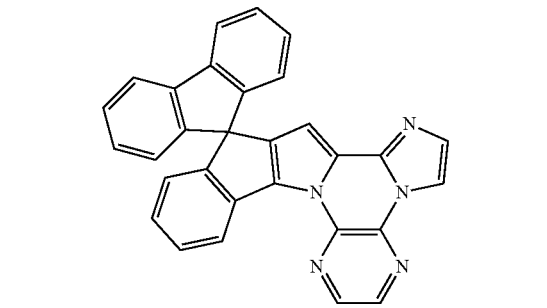
a
S2: heating the Compound a and the compound Y-L-Ar, Pd(OAc)$_2$, PPh$_3$, K$_2$CO$_3$ and DMAc to 150° C. to react under a nitrogen atmosphere to obtain the compound represented by Formula (I).

The Y is chlorine or bromine.

The preparation method of the Compound a is as follows:
A) reacting Compound a-1 with o-dihalopyrazine to obtain Compound a-2;
B) reacting the Compound a-2 with imidazole to obtain Compound a-3;
C) cyclizing the Compound a-3 to obtain Compound a.

The reaction Formula (I)s as follows:

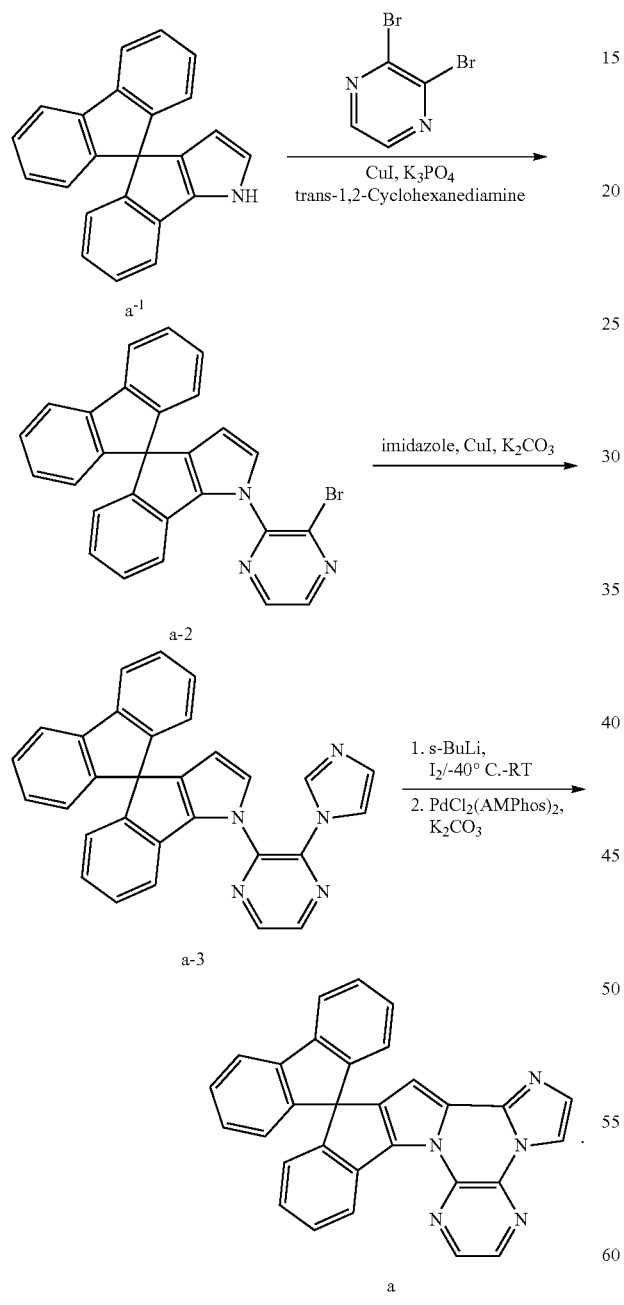

The above-mentioned compounds are applied to organic electroluminescent devices, mechanoluminescent devices, organic field effect transistors, organic solar cells and chemical sensors.

The organic electroluminescent device according to the invention includes a cathode, an anode, and an organic layer. The organic layer is one or more of a hole injection layer, a hole transport layer, a light-emitting layer, a hole-blocking layer, an electron injection layer, and an electron transport layer, each of which need not be incorporated in the organic layer.

At least one of the hole injection layer, hole transport layer, hole-blocking layer, light-emitting layer and/or electron transport layer contains the compound represented by Formula (I).

Preferably, the layer where the compound represented by Formula (1) is located is a light-emitting layer or an electron transport layer.

The total thickness of the device's organic layer according to the invention is 1-1000 nm, preferably 1-500 nm, and more preferably 5-300 nm.

The organic layer can be formed into a thin film by vapor deposition or solution method.

As the experimental results showed, compared with the common light-emitting material CBP transporting holes easily, the organic light-emitting material according to the invention has better thermal stability and balanced carrier transport performance, as well as can improve the luminous efficiency and color purity, with the potential to be applied to organic electroluminescent devices.

BRIEF DESCRIPTION OF THE DRAWING

The FIGURE is a structural diagram of the organic electroluminescent device according to invention.

10—glass substrate, 20—anode, 30—hole injection layer, 40—hole transport layer, 50—light-emitting layer, 60—electron transport layer, 70—electron injection layer, 80—cathode.

DETAILED DESCRIPTION OF THE PREFERRED EMBODIMENTS

In order to describe the invention in more detail, the following examples are given, but not limited thereto.

Compound 1-1 and Compound 13-1 that are not specifically mentioned are commercially available compounds.

Example 1

Synthetizing Compound 1

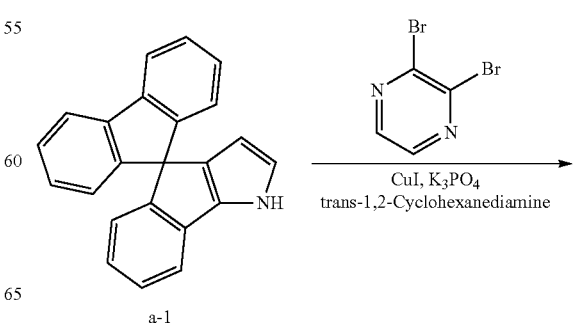

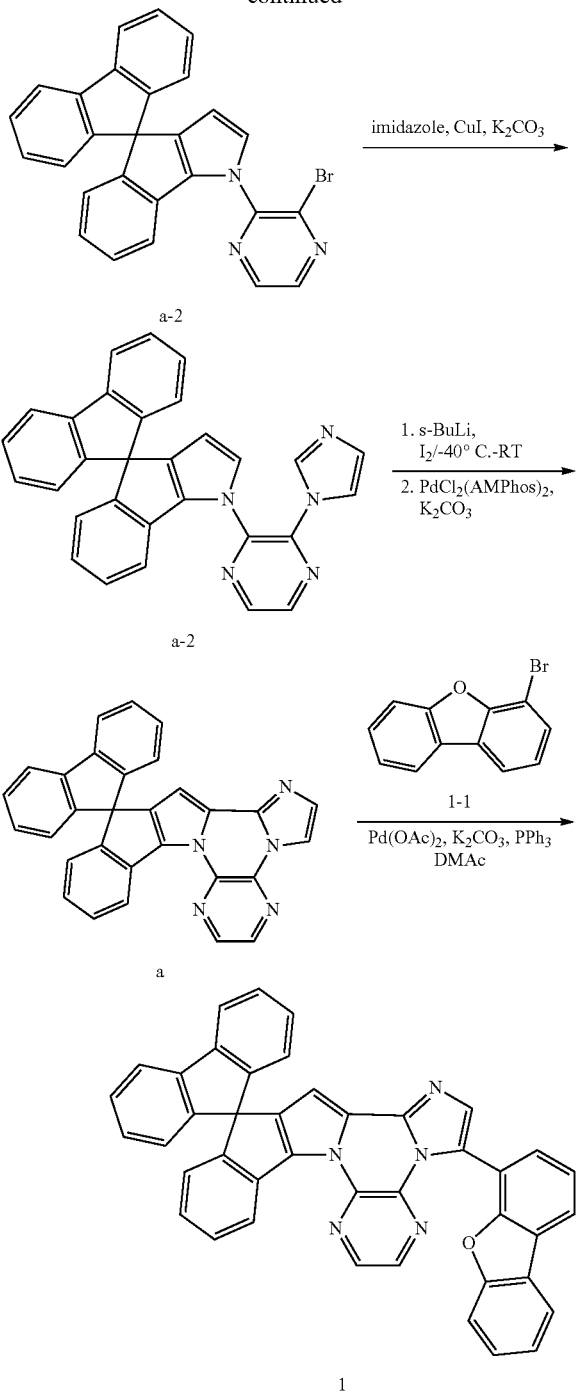

Synthetizing Intermediate a-2

The Compound a-1 (6.10 g, 20.0 mmol) (synthesized by reference to Literature Org. Lett., 2010, 12, 296-299), o-dibromobenzene (9.44 g, 40.0 mmol), CuI (380 mg, 2.0 mmol), trans-1,2-cyclohexanediamine (456 mg, 4.0 mmol), $K_3PO_4$ (12.74 g, 60.0 mmol) and xylene (100 mL) are sequentially added to the Schlenk tube under a nitrogen atmosphere, heated to 90° C. and react for 24 hours. After cooling to room temperature, the above reaction solution is added to water, extracted by dichloromethane three times, and then organic phases are combined. After the organic phase is dried by anhydrous sodium sulfate, and spun off the solvent, and the residue is separated by column chromatography to obtain a grayish white solid (5.1 g, the yield is 55%).

Synthetizing Intermediate a-3

The Compound a-2 (5.0 g, 10.9 mmol), imidazole (1.36 g, 20.0 mmol), CuI (380 mg, 2.0 mmol), $K_2CO_3$ (8.50 g, 40.0 mmol) and xylene (100 mL) are sequentially added to the Schlenk tube under a nitrogen atmosphere, heated to 90° C. and react for 24 hours. After cooling to room temperature, the above reaction solution is added to water, extracted by dichloromethane three times, and then organic phases are combined. After the organic phase is dried by anhydrous sodium sulfate, and spun off the solvent, and the residue is separated by column chromatography to obtain a light yellow solid (3.2 g, the yield is 66%).

Synthetizing Intermediate a

The Compound a-3 (3.0 g, 6.7 mmol) is dissolved in tetrahydrofuran (30 mL) under a nitrogen atmosphere, and cooled to −40° C., then added to by sec-butyllithium s-BuLi (1.2 eq) dropwise with stirring for 30 minutes, then iodine (1.1 eq) is added, after stirring for 30 minutes, the temperature thereof rises to room temperature, then stirring continues for 1 hour. The above reaction solution is added to water, extracted by dichloromethane three times, and then organic phases are combined. After the organic phase is dried by anhydrous sodium sulfate, and spun off the solvent to obtain a light yellow solid. The above solid is dis solved in tetrahydrofuran (20 mL), dichlorodi-tert-butyl(4-Dimethylaminophenyl)-phosphine palladium $PdCl_2(AMPhos)_2$ (0.05 eq) and potassium carbonate aqueous solution (2M, 4 mL) are added, and refluxed overnight under a nitrogen atmosphere. After cooling to room temperature, the above reaction solution is added to water, extracted by dichloromethane three times, and then organic phases are combined. After the organic phase is dried by anhydrous sodium sulfate, and spun off the solvent, and the residue is separated by column chromatography to obtain a light yellow solid (1.6 g, the yield is 53%).

Synthetizing Compound 1

The Compound a (2.1 g, 4.7 mmol), Compound 1-1 (5.8 g, 23.4 mmol), $Pd(OAc)_2$ (105 mg, 0.47 mmol), $PPh_3$ (380 mg, 1.4 mmol), $K_2CO_3$ (1.38 g, 10 mmol) and DMAc (20 mL) are sequentially added to the Schlenk tube under a nitrogen atmosphere, heated to 150° C. and react for 24 hours. After cooling to room temperature, the above reaction solution is added to water, extracted by dichloromethane three times, and then organic phases are combined. After the organic phase is dried by anhydrous sodium sulfate, and spun off the solvent, and the residue is separated by column chromatography to obtain a light yellow solid (1.5 g, the yield is 52%). ESI-MS (m/z): 614.3 (M+1).

Example 2

Synthetizing Compound 9

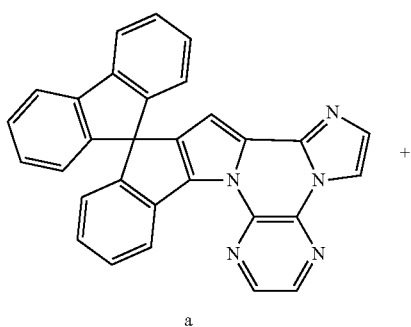

-continued

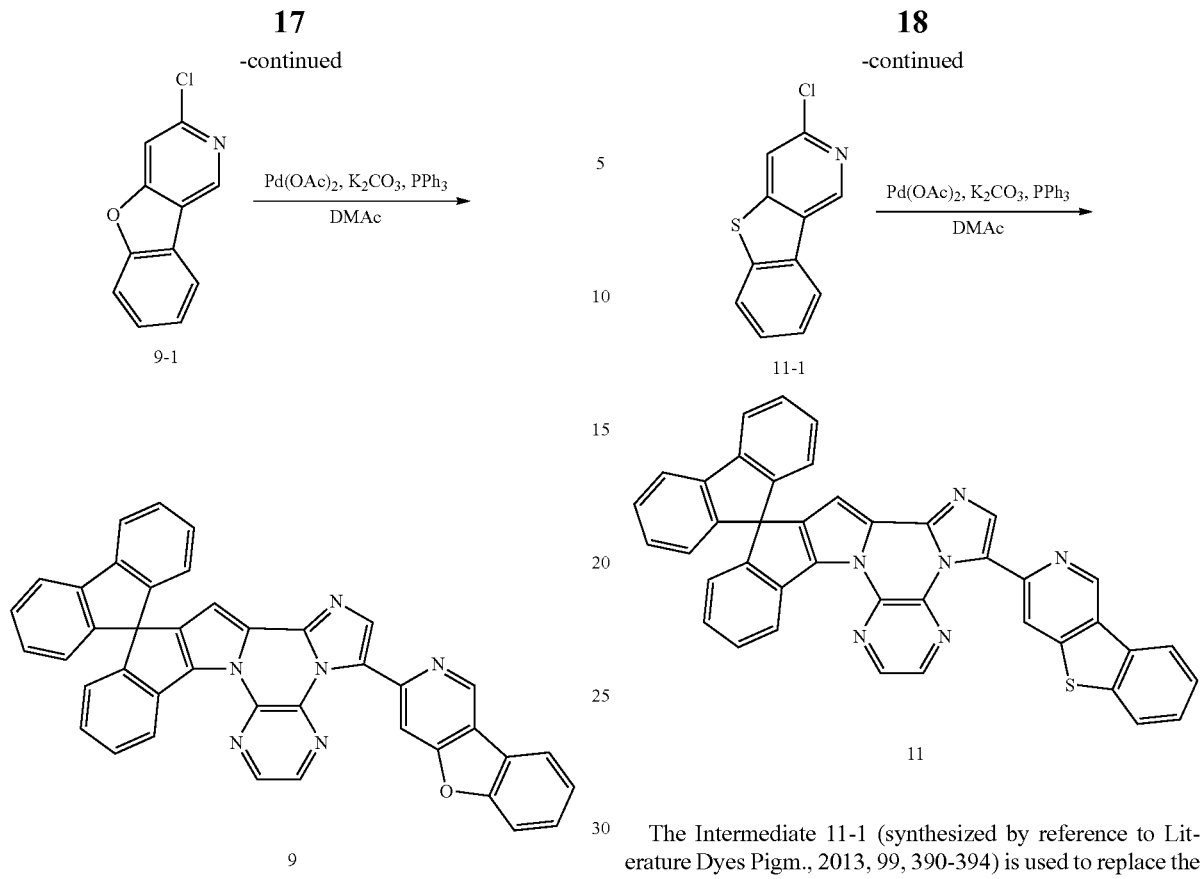

9

The Compound a (1.6 g, 3.6 mmol), the Compound 9-1 (3.7 g, 18.0 mmol) (synthesized by reference to CN102449107), Pd(OAc)$_2$ (80 mg, 0.36 mmol), PPh$_3$ (190 mg, 0.72 mmol), K$_2$CO$_3$ (1.38 g, 10 mmol) and DMAc (20 mL) are sequentially added to the Schlenk tube under a nitrogen atmosphere, heated to 150° C. and react for 24 hours. After cooling to room temperature, the above reaction solution is added to water, extracted by dichloromethane three times, and then organic phases are combined. After the organic phase is dried by anhydrous sodium sulfate, and spun off the solvent, and the residue is separated by column chromatography to obtain a light yellow solid (700 mg, the yield is 32%). ESI-MS (m/z): 615.0 (M+1).

Example 3

Synthetizing Compound 11

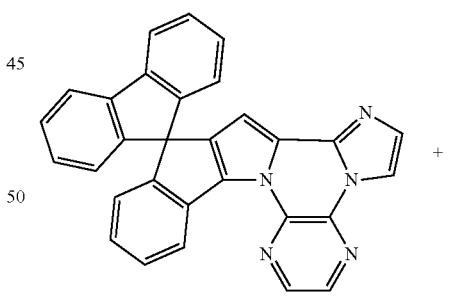

-continued

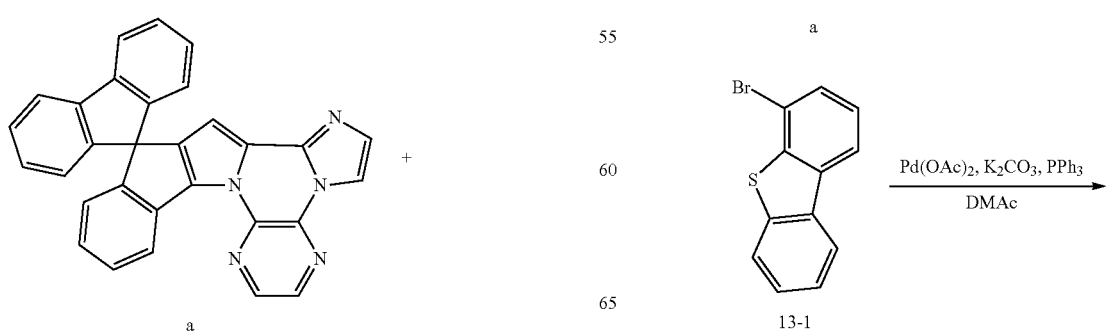

11

The Intermediate 11-1 (synthesized by reference to Literature Dyes Pigm., 2013, 99, 390-394) is used to replace the Intermediate 9-1, and the Compound 11 is prepared by reference to the method for synthetizing the Compound 9 to obtain a light yellow solid (700 mg, the yield is 33%). ESI-MS (m/z): 631.3 (M+1).

Example 4

Synthetizing Compound 13

-continued

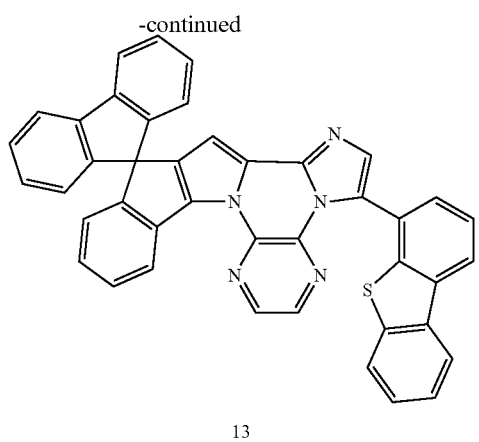

13

The Intermediate 13-1 is used to replace the Intermediate 9-1, and the Compound 13 is prepared by reference to the method for synthetizing the Compound 9 to obtain a light yellow solid (1.1 g, the yield is 50%). ESI-MS (m/z): 630.0 (M+1).

Example 5

Synthetizing Compound 22

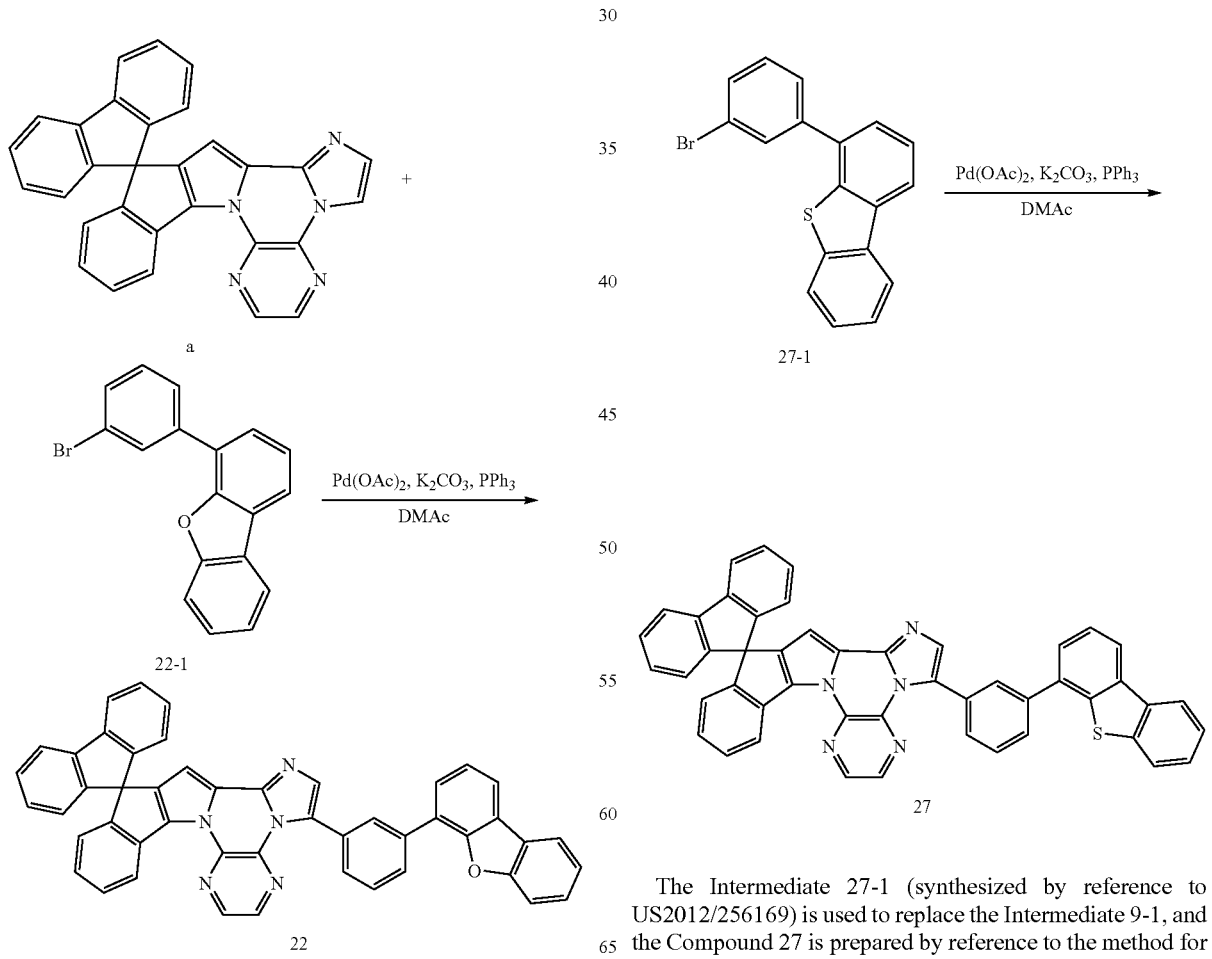

The Intermediate 22-1 (synthesized by reference to CN105585555) is used to replace Intermediate 9-1, and the Compound 22 is prepared by reference to the method for synthetizing the Compound 9 to obtain a light yellow solid (800 mg, the yield is 47%). ESI-MS (m/z): 690.0 (M+1).

Example 6

Synthetizing Compound 27

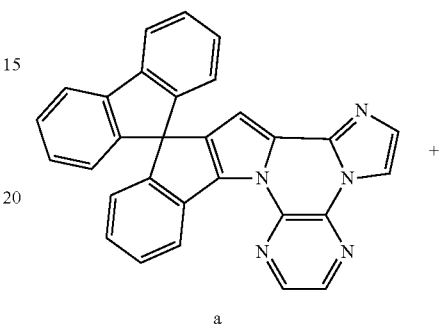

The Intermediate 27-1 (synthesized by reference to US2012/256169) is used to replace the Intermediate 9-1, and the Compound 27 is prepared by reference to the method for synthetizing the Compound 9 to obtain a light yellow solid (600 mg, the yield is 50%). ESI-MS (m/z): 706.2 (M+1).

Example 7

Synthetizing Compound 30

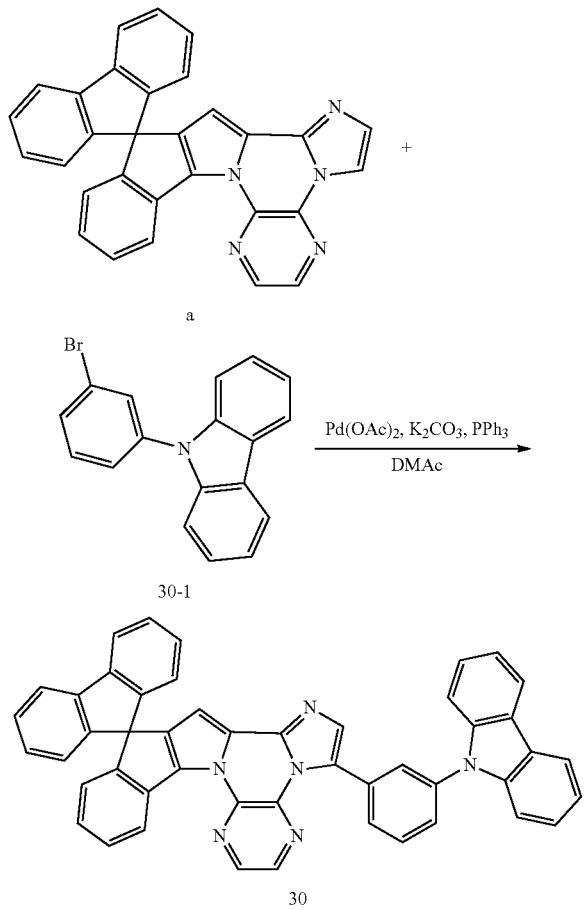

The Intermediate 30-1 (synthesized by reference to CN107686484) is used to replace the Intermediate 9-1, and the Compound 30 is prepared by reference to the method for synthetizing the Compound 9 to obtain a light yellow solid (750 mg, the yield is 43%). ESI-MS (m/z): 689.3 (M+1).

Example 8

Synthetizing Compound 36

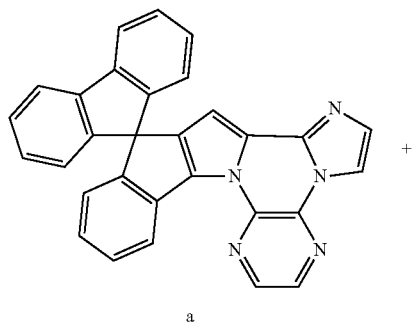

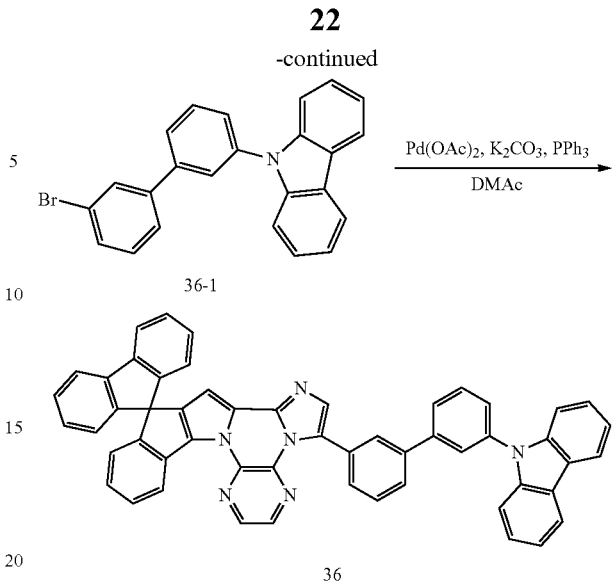

The Intermediate 36-1 (synthesized by reference to Literature Chem. Mater., 2013, 25, 3758-3765) is used to replace the Intermediate 9-1, and the Compound 36 is prepared by reference to the method for synthetizing the Compound 9 to obtain a light yellow solid (660 mg, the yield is 52%). ESI-MS (m/z): 765.1 (M+1).

Examples 9-16

The organic light-emitting material according to the invention is used to prepare an electroluminescent device, the structure of which is shown in the FIGURE.

First, washing the transparent conductive ITO glass substrate 10 (with an anode 20 on it) sequentially by detergent solution, deionized water, ethanol, acetone, and deionized water, and then treating it with oxygen plasma for 30 seconds.

Then, evaporatively depositing 10 nm thick HATCN on the ITO as the hole injection layer 30.

Then, evaporatively depositing the compound TAPC to form a 40 nm thick hole transport layer 40.

Then, evaporatively depositing a 30 nm thick light-emitting layer 50 on the hole transport layer. The light-emitting layer is composed of Ir(PPy)$_3$ (10%) and the compound product (90%) in Examples 1-8 by co-doping.

Then, evaporatively depositing a 50 nm thick TmPyPb on the light-emitting layer as the electron transport layer 60.

Finally, evaporatively depositing a 1 nm thick LiF as the electron injection layer 70 and a 100 nm thick Al as the device cathode 80.

Comparative Example

CBP is used to replace the above-mentioned compound in the invention, an organic light-emitting device is prepared according to the same method.

The structure presented in the device is as bellows.

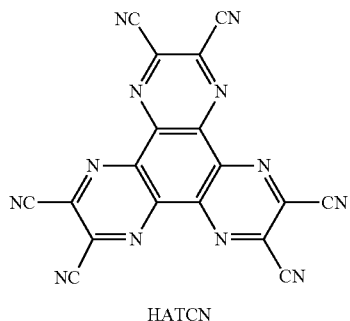

HATCN

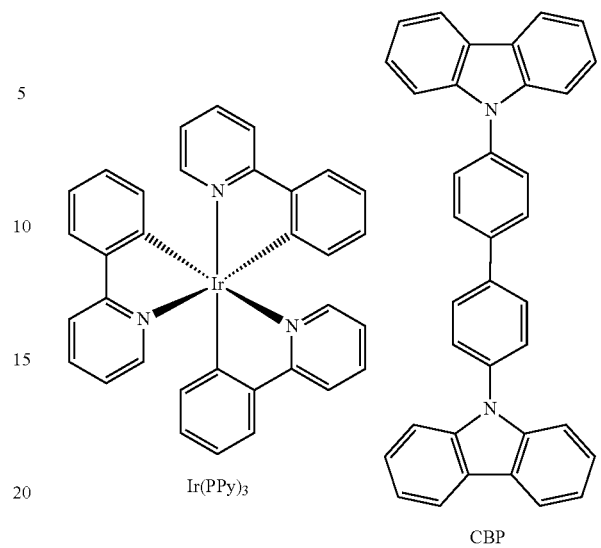

Ir(PPy)₃

CBP

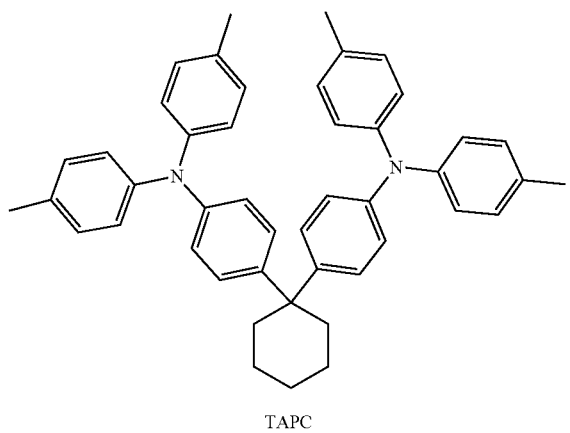

TAPC

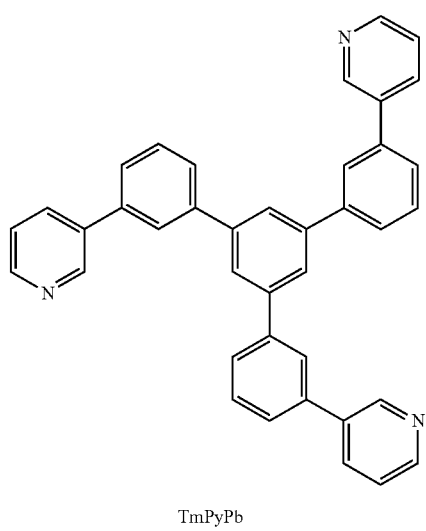

TmPyPb

The efficiency of the organic electroluminescent devices in Examples 9-17 and Comparative Example at a current density of 10 mA/cm² is as follows:

| Light-emitting device | Compound | External quantum efficiency | Luminous color |
|---|---|---|---|
| 9 | 1 | 15.6 | Green |
| 10 | 9 | 14.7 | Green |
| 11 | 11 | 14.5 | Green |
| 12 | 13 | 15.2 | Green |
| 13 | 22 | 16.4 | Green |
| 14 | 27 | 16.2 | Green |
| 15 | 30 | 16.8 | Green |
| 16 | 36 | 17.2 | Green |
| Comparative Example | CBP | 12.7 | Green |

Under the same conditions, the efficiency of organic electroluminescent devices prepared by using the compound of the invention is better than that of the comparative example. The compound of the invention has better stability, and the device manufactured by using the compound of the invention has better color purity and efficiency, with great significance for optimizing the performance of organic optoelectronic devices.

The various embodiments described above are only examples, and are not intended to limit the scope of the invention. Without departing from the essence of the invention, various materials and structures in the invention can be replaced by other materials and structures. It should be understood that a skilled person in the art can make many modifications and changes according to the idea of the invention without creative effort. Therefore, the technical solutions that can be obtained by the skilled person through analysis, ratiocination or partial research on the basis of the prior art should be within the protection scope defined by the claims.

What is claimed is:

1. An organic electroluminescent material having a chemical structure of Formula (I),

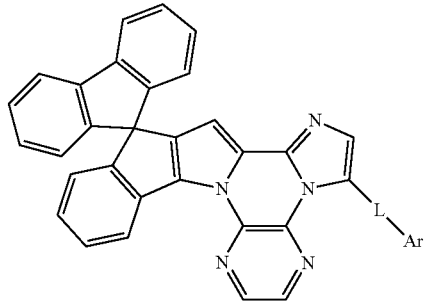
(I)

wherein:
L is a single bond, a substituted or unsubstituted phenylene group, a substituted or unsubstituted biphenylene group, or a substituted or unsubstituted pyridylene group, Ar is one of the following groups:

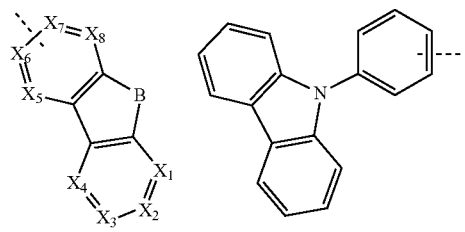

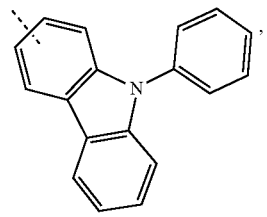

B is selected from O, S and Se, and
X1-X8 are independently selected from N or CR, and each six-membered ring contains at most one N atom, R is independently selected from one of a hydrogen atom, a deuterium atom, a halogen, an alkyl group, a heteroalkyl group, an aryl group, a heteroaryl group, an aryloxy group.

2. The organic electroluminescent material according to claim 1, wherein:
L is a single bond, a substituted or unsubstituted phenylene group, a substituted or unsubstituted biphenylene group, or a substituted or unsubstituted pyridylene group,
Ar is one of the following groups:

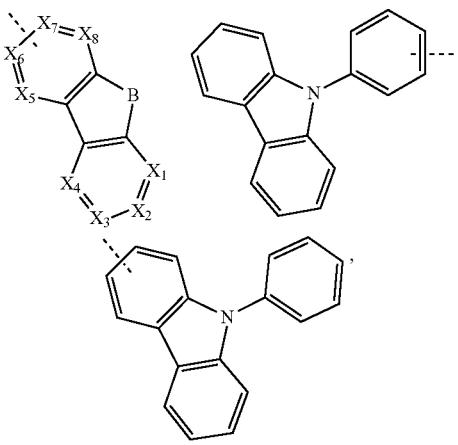

where B is selected from O and S, and
X1-X8 are independently selected from N or CR, and each six-membered ring contains at most one N atom, R is independently selected from one of a hydrogen atom, a deuterium atom, an alkyl group, and an aryl group.

3. The organic electroluminescent material according to claim 2, wherein:
L is a single bond or a phenylene group,
Ar is one of the following groups:

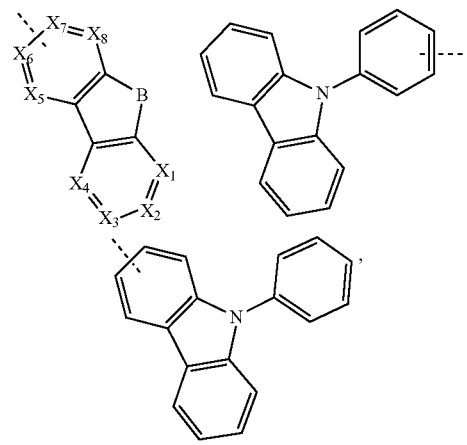

where B is selected from O and S, and
one of $X_1$-$X_8$ is N, and the rest are CH.

4. The organic electroluminescent material according to claim 3, wherein:
L is a single bond,
Ar is one of the following groups:

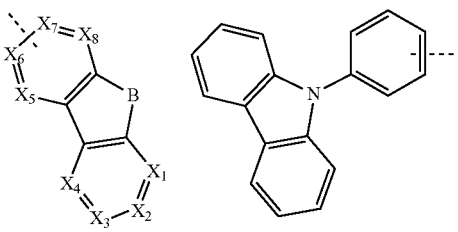

-continued

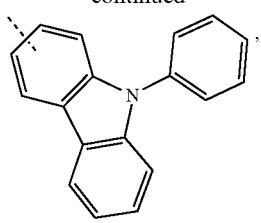

where B is selected from O and S, and one of $X_1$-$X_8$ is N, and the rest are CH.

5. The organic electroluminescent material according to claim 2, wherein:

L is a single bond,

Ar is one of the following groups:

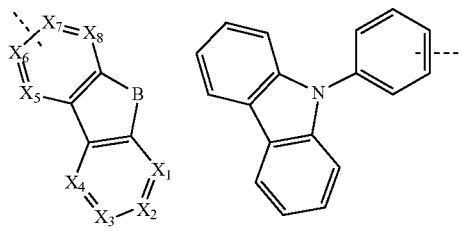

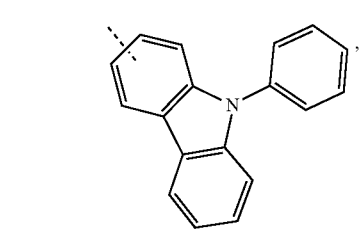

where B is selected from O and S, and $X_1$-$X_8$ are CH.

6. An organic electroluminescent device comprising:

a cathode, an anode, and an organic layer, wherein:

said organic layer is one or more of a hole injection layer, a hole transport layer, a light-emitting layer, a hole-blocking layer, an electron injection layer, and an electron transport layer, and said organic layer contains said organic electroluminescent material according to claim 2.

7. The organic electroluminescent device according to claim 6, wherein the layer in which said organic electroluminescent material is located is a light-emitting layer or an electron transport layer.

8. An organic electroluminescent material according to claim 1, comprising at least one of the following compounds:

1

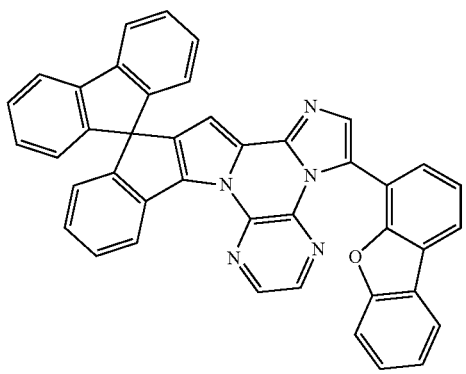

2

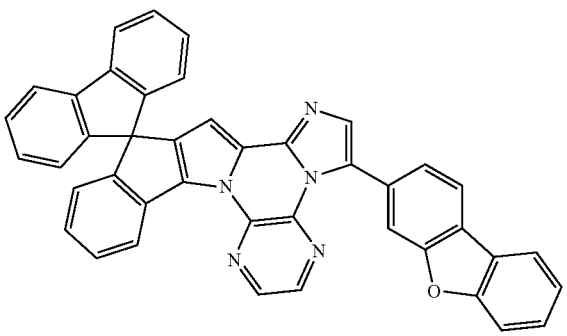

3

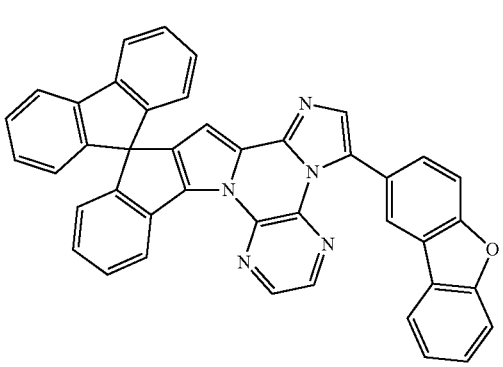

4

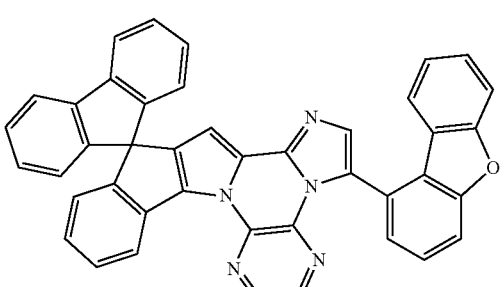

-continued
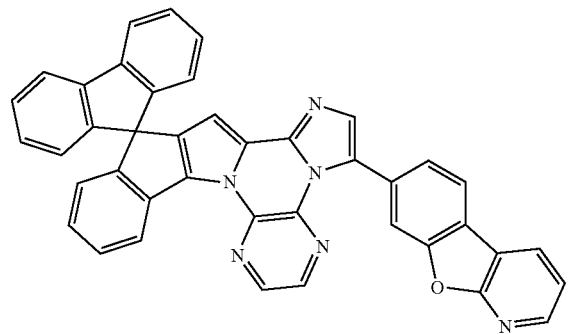
5
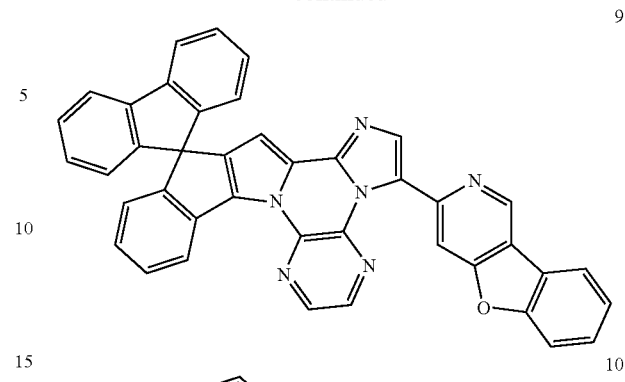
9
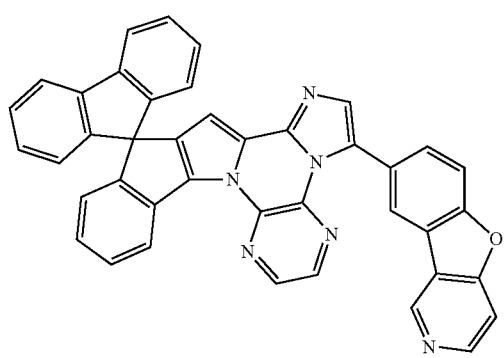
6
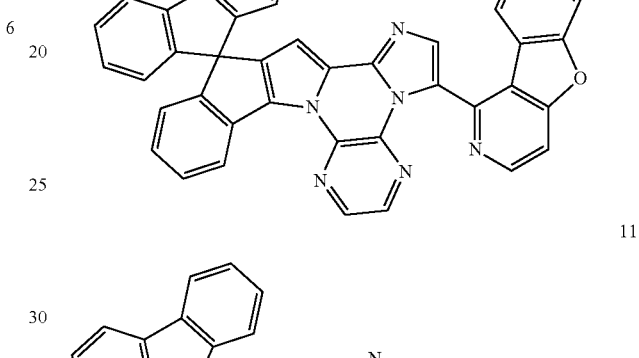
10
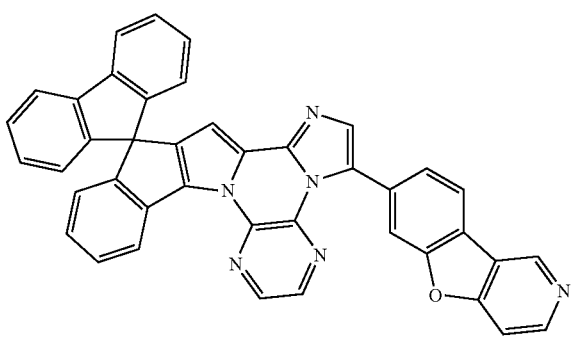
7
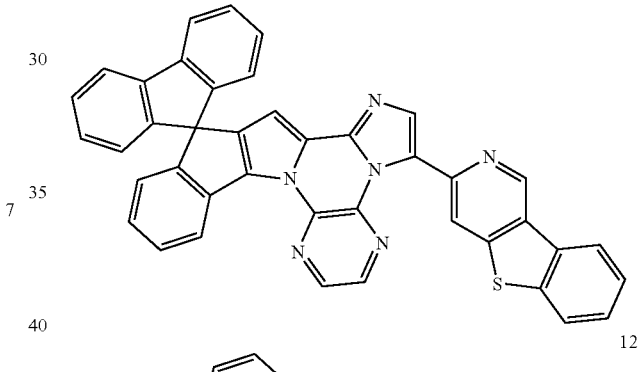
11
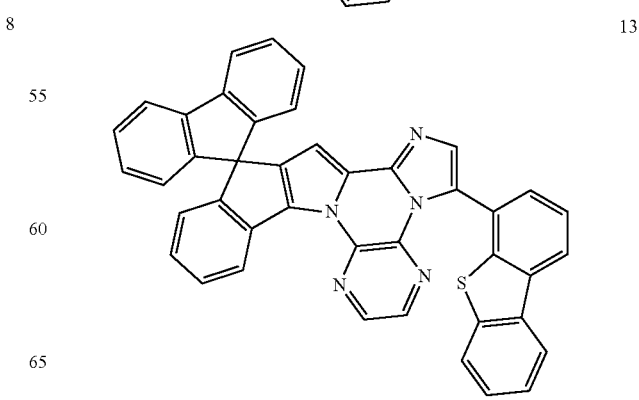
12
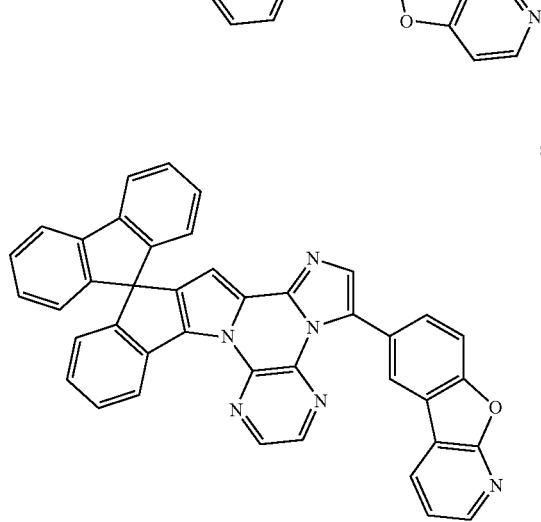
8
13

14
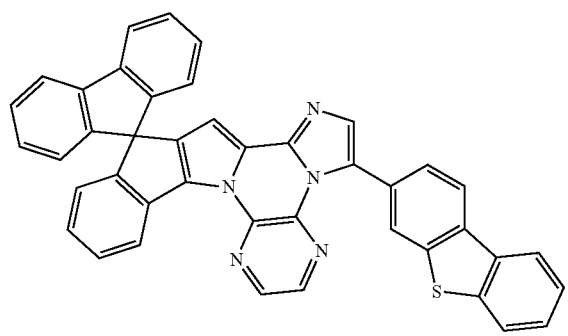
15
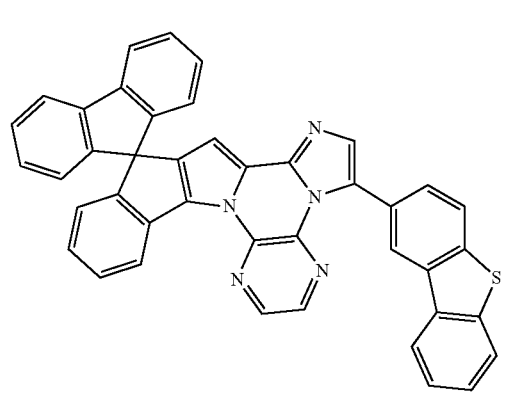
16
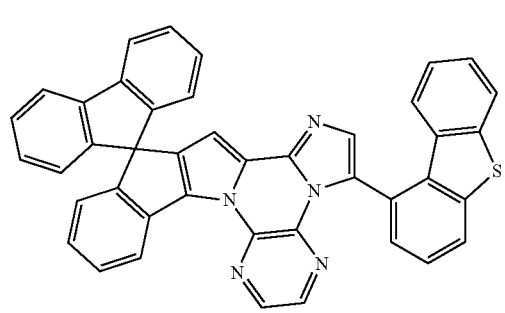
17
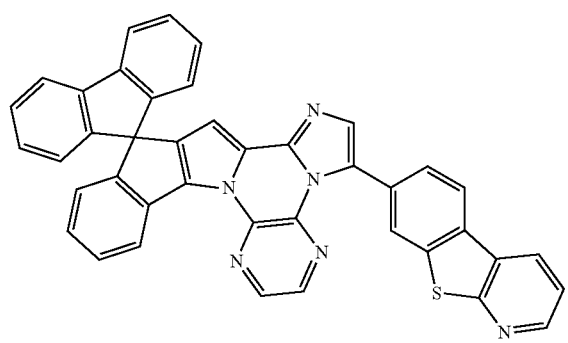
18
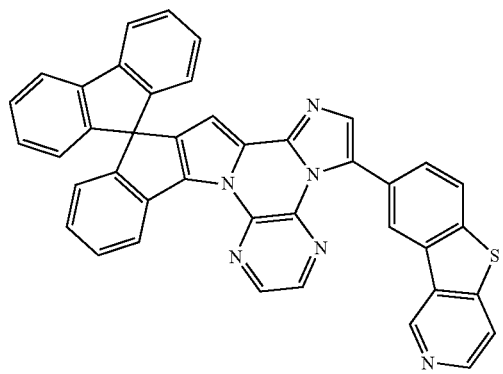
19
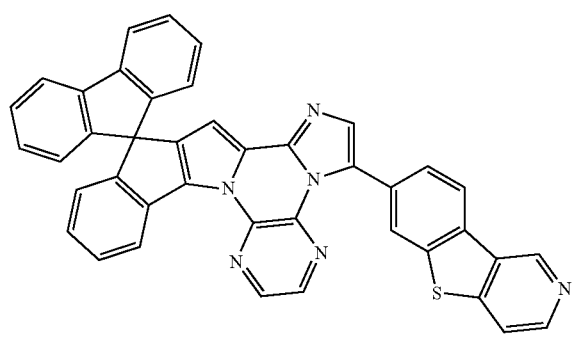
20
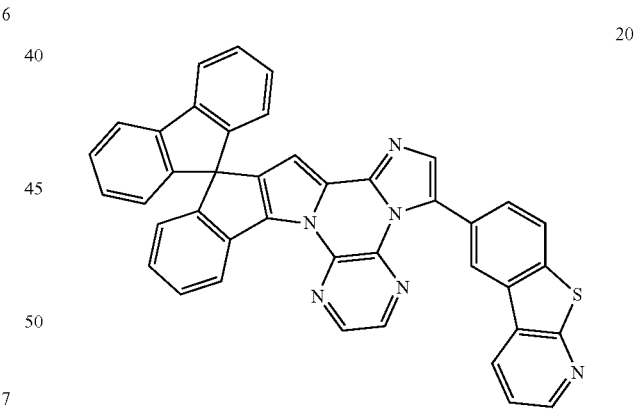
21
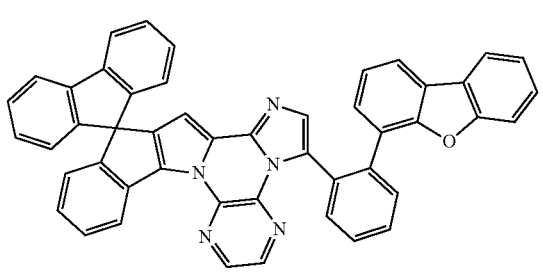

22
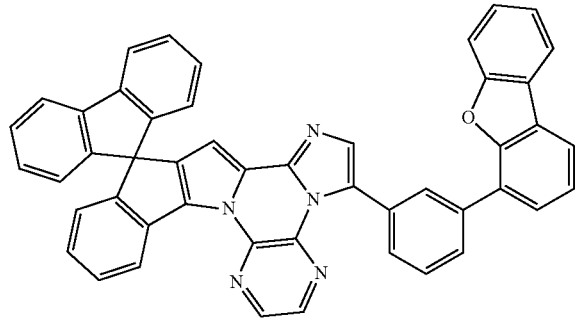
23
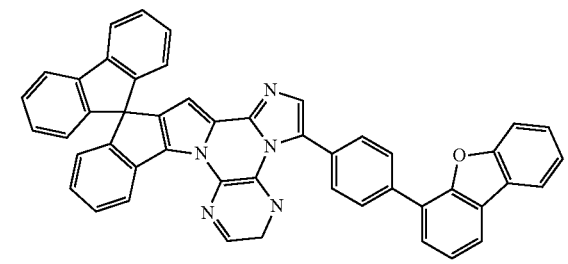
24
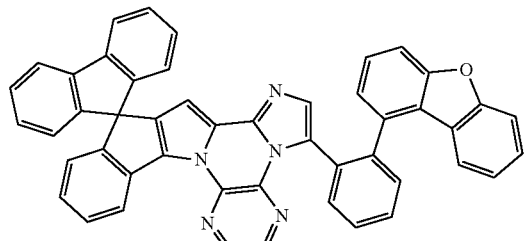
25
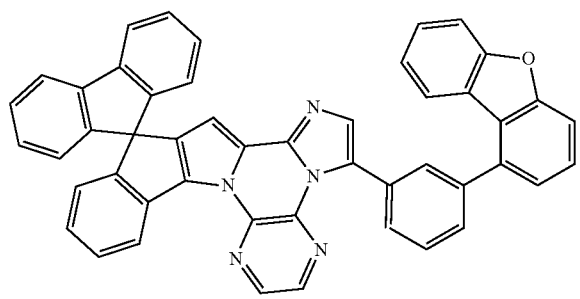
26
27
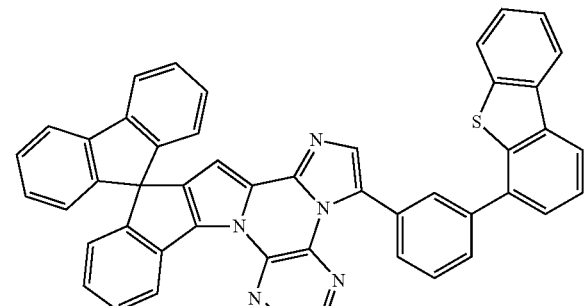
28
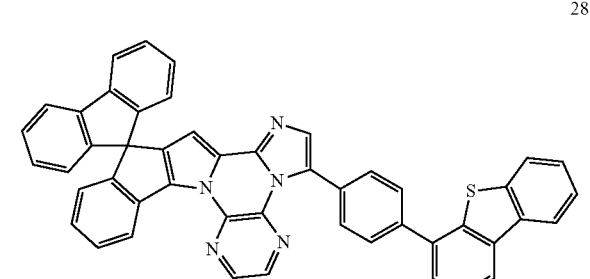
29
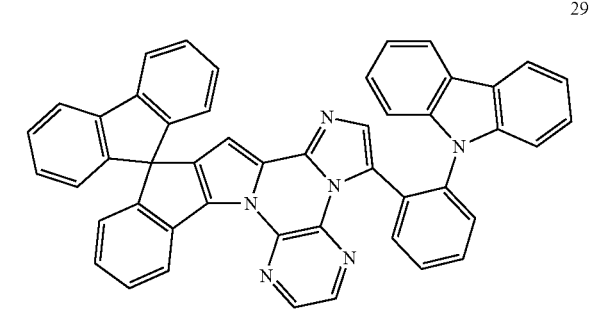
30
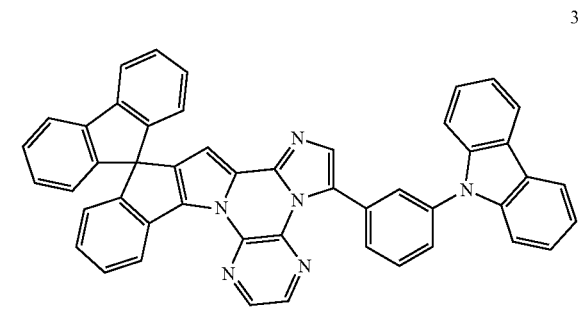
31
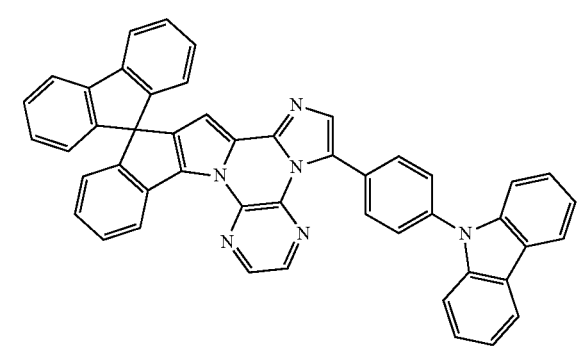

-continued

32
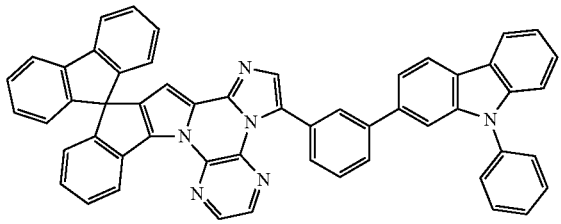

33
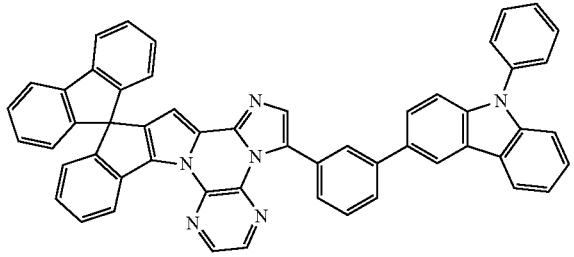

34
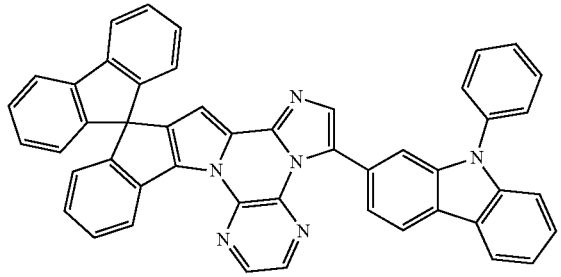

35
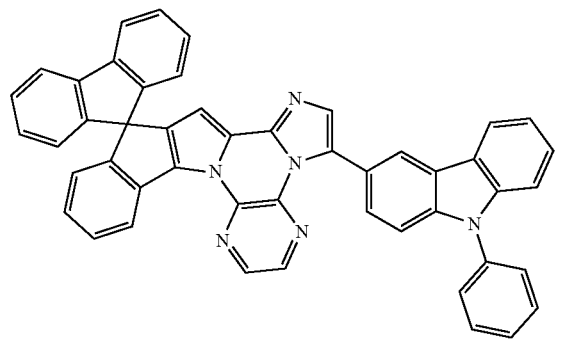

36
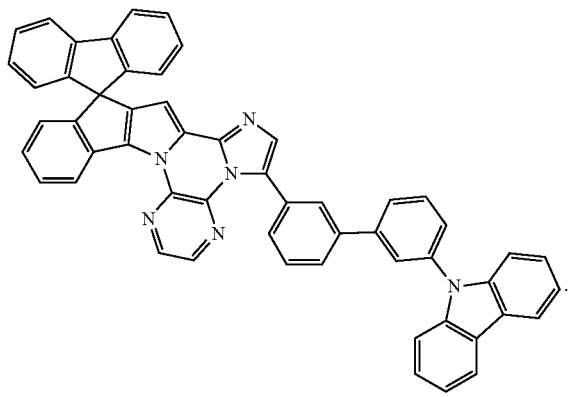

9. An organic electroluminescent device comprising:
a cathode,
an anode, and
an organic layer,
wherein:
said organic layer is one or more of a hole injection layer, a hole transport layer, a light-emitting layer, a hole-blocking layer, an electron injection layer, and an electron transport layer, and
said organic layer contains said organic electroluminescent material according to claim 8.

10. A preparation method for said organic electroluminescent material according to claim 1, comprising:
S1: providing Compound a and Y-L-Ar, where Y is halogen;

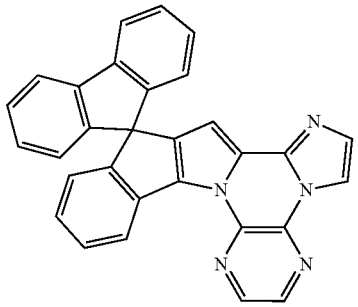
a (I)
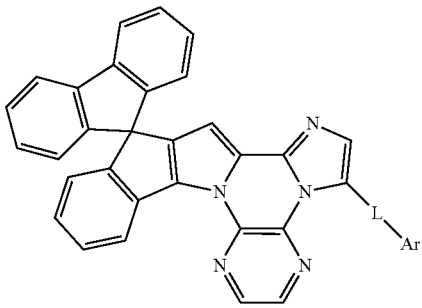

S2: heating said Compound a and Y-L-Ar, Pd(OAc)$_2$, PPh$_3$, K$_2$CO$_3$ and DMAc to 150° ° C. to react under a nitrogen atmosphere to obtain said compound represented by Formula (I).

11. The preparation method according to claim 10, wherein said Y is chlorine or bromine.

12. The preparation method according to claim 10, wherein the preparation method of said Compound a comprises the following steps:
A) reacting Compound a-1 with o-dihalopyrazine to obtain Compound a-2,
B) reacting said Compound a-2 with imidazole to obtain Compound a-3, and
C) cyclizing said Compound a-3 to obtain said Compound a,

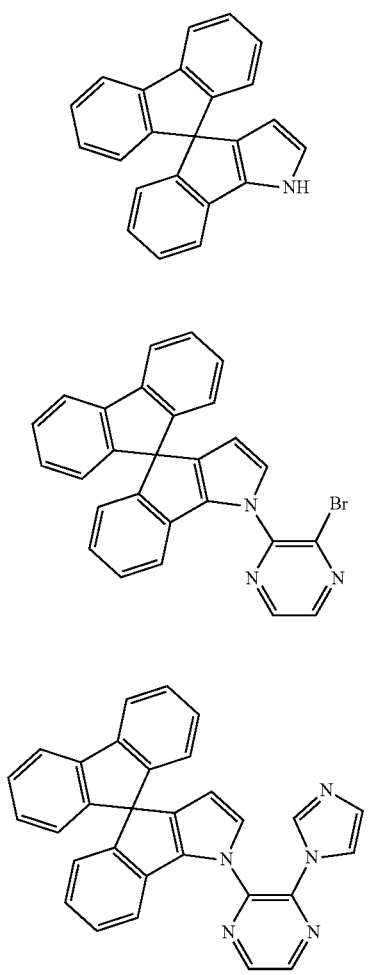

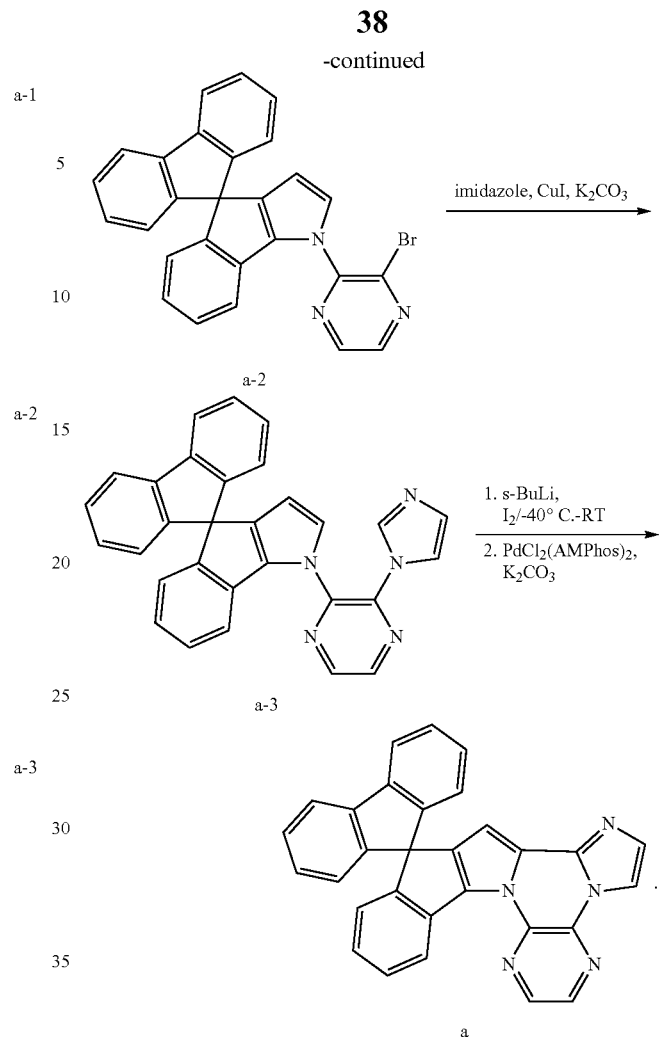

13. The preparation method according to claim 12, wherein said o-dihalopyrazine is o-dibromopyrazine.

14. The preparation method according to claim 13, wherein the reaction formula for preparing said Compound a is as follows:

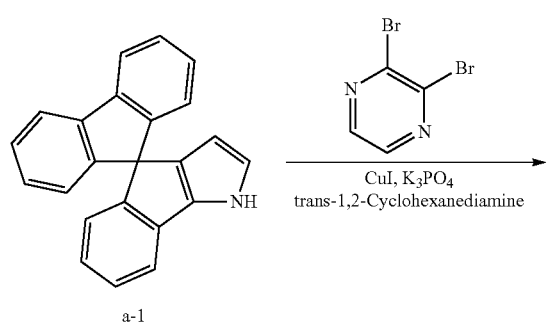

15. An organic electroluminescent device comprising:
a cathode,
an anode, and
an organic layer,
wherein:
   said organic layer is one or more of a hole injection layer, a hole transport layer, a light-emitting layer, a hole-blocking layer, an electron injection layer, and an electron transport layer, and
   said organic layer contains said organic electroluminescent material according to claim 1.

16. The organic electroluminescent device according to claim 15, wherein the layer in which said organic electroluminescent material is located is a light-emitting layer or an electron transport layer.

17. The organic electroluminescent device according to claim 15, wherein:
   the total thickness of said organic layer is 1-1000 nm, and
   said organic layer is formed into a thin film by vapor deposition or solution method.

* * * * *